US00PP24824P2

(12) United States Plant Patent
Smith

(10) Patent No.: US PP24,824 P2
(45) Date of Patent: Aug. 26, 2014

(54) ***CHRYSANTHEMUM* PLANT NAMED 'CIFZ0006'**

(50) Latin Name: *Chrysanthemum×morifolium*
Varietal Denomination: CIFZ0006

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 120 days.

(21) Appl. No.: 13/694,119

(22) Filed: Oct. 31, 2012

(51) Int. Cl.
*A01H 5/00* (2006.01)

(52) U.S. Cl.
USPC ..... Plt./290

(58) Field of Classification Search
USPC ..... Plt./290
See application file for complete search history.

*Primary Examiner* — Wendy C Haas
(74) *Attorney, Agent, or Firm* — Joshua L. Price

(57) ABSTRACT

A new *Chrysanthemum* plant named 'CIFZ0006' particularly distinguished by the medium sized decorative-type inflorescences with bicolored greyed-red ray floret color, medium to large sized and round plant habit with a natural season flowering response of mid-late September.

1 Drawing Sheet

Latin name of the genus and species of the plant claimed: *Chrysanthemum×morifolium.*

Varietal denomination: 'CIFZ0006'.

BACKGROUND OF THE NEW PLANT

The present invention comprises a new *Chrysanthemum*, botanically known as *Chrysanthemum×morifolium*, and hereinafter referred to by the variety name 'CIFZ0006'.

'CIFZ0006' is a product of a planned breeding program. The new cultivar has medium sized decorative-type inflorescences with bicolored greyed-red ray floret color, medium to large sized and round plant habit with a natural season flowering response of mid-late September.

'CIFZ0006' originates as a whole plant mutation of an unnamed mutation designated as '05-M162A'. 'CIFZ0006' was discovered and selected by the inventor in November 2009 as a single flowering plant within a population of the parent cultivar grown in pots outdoors in Alva, Fla. The parent cultivar '05-M162A' has light lavender inflorescence color and a natural season flowering response time that is 2-5 days slower than that of 'CIFZ0006'.

The first act of asexual reproduction of 'CIFZ0006' was accomplished when vegetative cuttings were propagated from the initial selection in January 2010 in a greenhouse in Alva, Fla.

BRIEF SUMMARY OF INVENTION

Horticultural examination of plants grown from cuttings of the plant initiated in January 2010, and continuing thereafter, has demonstrated that the combination of characteristics as herein disclosed for 'CIFZ0006' are firmly fixed and are retained through successive generations of asexual reproduction.

'CIFZ0006' has not been observed under all possible environmental conditions. The phenotype may vary significantly with variations in environment such as temperature, light intensity, and day length.

Plant Breeder's Rights for this cultivar were applied for in Canada on Feb. 24, 2012 (12-7525) and at the Community Plant Variety Office on May 10, 2012 (2012/1025). 'CIFZ0006' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0006' with colors being as true as possible with an illustration of this type. The photographic drawing shows a flowering plant of the new variety, and a close-up of a mature inflorescence.

DETAILED BOTANICAL DESCRIPTION

The plant descriptions, measurements and aforementioned photographs were taken in Gilroy, Calif. in early August 2012 outdoors. These plants were about 12-14 weeks of age grown in 1 gallon pots in an outdoor trial.

Color references are made to The Royal Horticultural Society Colour Chart (R.H.S.) 2001.

TABLE 1

DIFFERENCES BETWEEN THE NEW VARIETY 'CIFZ0006' AND A MOST SIMILAR VARIETY

| | 'CIFZ0006' | 'Zesty Yovictoria' (U.S. Plant Pat. No, 15,323) |
|---|---|---|
| Blackcloth and natural season response: | Few days slower | Few days faster |
| Inflorescence size: | Larger | Smaller |
| Inflorescence color: | Lighter shades | Deeper shades |
| Disc floret quantity: | More | Fewer |

Plant:

*Form, growth and habit.*—Herbaceous garden-type, stems upright and outwardly spreading, freely branching, strong and moderately vigorous growth habit.

*Plant height.*—18-20.0 cm.

*Plant height (inflorescence included).*—27-30.0 cm.

*Plant width.*—38-41.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A. Lower surface: Closest to RHS 137C.

*Mature, leaf color, upper surface.*—Closest to RHS 137A. Lower surface: Closest to RHS 137C.

*Length.*—2.2-3.4 cm.

*Width.*—3.1-4.0 cm.

*Shape.*—Ovate.

*Base shape.*—Attenuate.

*Apex shape.*—Acute to slightly mucronulate.

*Margin.*—Palmately lobed; dentate.

*Texture, upper surface.*—Bifid T-shaped hairs. Lower surface: Bifid T-shaped hairs.

*Color of veins, upper surface.*—RHS 146C.

*Color of veins, lower surface.*—RHS 146C.

*Pattern of veining.*—Palmate.

*Petiole color.*—RHS 146C.

*Length.*—1-1.3 cm.

*Diameter.*—0.2 cm.

*Texture.*—Bifid T-shaped hairs.

Stem:

*Quantity of main branches per plant.*—8-10.

*Color of stem.*—Closest to RHS 137A but a little brighter green.

*Length of stem.*—15-18.0 cm.

*Diameter.*—0.3-0.5 cm.

*Length of internodes.*—0.5-1.0 cm.

*Texture.*—Bifid T-shaped hairs.

*Color of peduncle.*—Closest to RHS 137A.

*Length of peduncle.*—8-9.0 cm.

*Peduncle diameter.*—0.2 cm.

*Texture.*—Bifid T-shaped hairs.

Inflorescence:

*Type.*—Solitary decorative-type inflorescences borne terminally above foliage, ray florets arranged acropetally on a capitulum.

*Quantity of short days to flowering (response time).*—About 48 days.

*Natural season flowering.*—Mid to late September.

*Quantity of inflorescences per plant.*—About 75 with an additional 100 buds.

*Lastingness of individual blooms on the plant.*—Little less than 6 weeks from the first color.

*Fragrance.*—Slightly spicy.

Bud (just when opening/showing color):

*Color.*—Varying hues of RHS 181C with some having more of a tan color.

*Length.*—0.9-1.1 cm.

*Width.*—1-1.1 cm.

*Shape.*—Oblate.

Immature inflorescence:

*Diameter.*—4-4.5 cm.

*Color of ray florets, upper surface.*—Light hues of RHS 180B to RHS 180C.

*Color of ray florets, lower surface.*—RHS 180D.

Mature inflorescence:

*Diameter.*—5.5-6.1 cm.

*Depth.*—1.5-1.8 cm.

*Total diameter of disc.*—0.3-0.4 cm.

*Receptacle color.*—RHS 144C.

*Receptacle height.*—0.4 cm.

*Receptacle diameter.*—0.4 cm.

Ray florets:

*Average quantity of florets.*—150 in several whorls.

*Color of florets, upper surface.*—Light shades of RHS 181C to RHS 181D with margins of RHS 181C; and all fading to less color and more RHS N155B to RHS 155B background color. Lower surface: Very lights shades of RHS 180D fading to mostly RHS N155B.

*Length.*—2.7-3.0 cm.

*Width.*—0.5-0.7 cm.

*Shape.*—Elliptical.

*Apex shape.*—Praemorse.

*Base shape.*—Cuneate.

*Margin.*—Entire.

*Texture, upper surface.*—Papillose. Lower surface: Papillose.

Disc florets:

*Average quantity of florets.*—1-15.

*Color of florets.*—RHS 1C with an RHS 13A apex.

*Length.*—0.35-0.4 cm.

*Width.*—0.1 cm.

*Shape.*—Tubular, elongated.

*Apex shape.*—Acute, 5 pointed.

*Texture, inner surface.*—Glabrous. Outer surface: Glabrous.

Phyllaries:

*Quantity.*—20.

*Color, upper surface.*—RHS 137C.

*Color, lower surface.*—RHS 137A.

*Length.*—0.9-1.1 cm.

*Width.*—0.17-0.25 cm.

*Shape.*—Lanceolate.

*Apex shape.*—Acute.

*Based.*—Fused.

*Margins.*—Entire.

*Texture, upper surface.*—Glabrous.

*Textures, lower surface.*—Bifid T-shaped hairs.

Reproductive organs:

*Gynoecium.*—Pistil: 1, found on both types of florets. Length: 0.5 cm. Style color: RHS 1C. Style length: 0.4 cm. Stigma color: RHS 13A. Stigma shape: Biparted. Ovary color: Not observed to date. Ovary length: Not observed to date. Ovary width: Not observed to date.

*Androecium.*—Stamens: 4, found on only on the disc florets. Color of filaments: RHS 155C. Length filaments: 0.2-0.3 cm. Anther color: RHS 15B. Anther length: 0.15 cm. Anther shape: Oval. Color of pollen: RHS 15A. Pollen amount: Normal.

*Fertility/seed set.*—Has not been observed to date.

*Disease/pest resistance.*—Has not been observed to date.

What is claimed is:

1. A new and distinct variety of *Chrysanthemum* plant named 'CIFZ0006' substantially as illustrated and described herein.

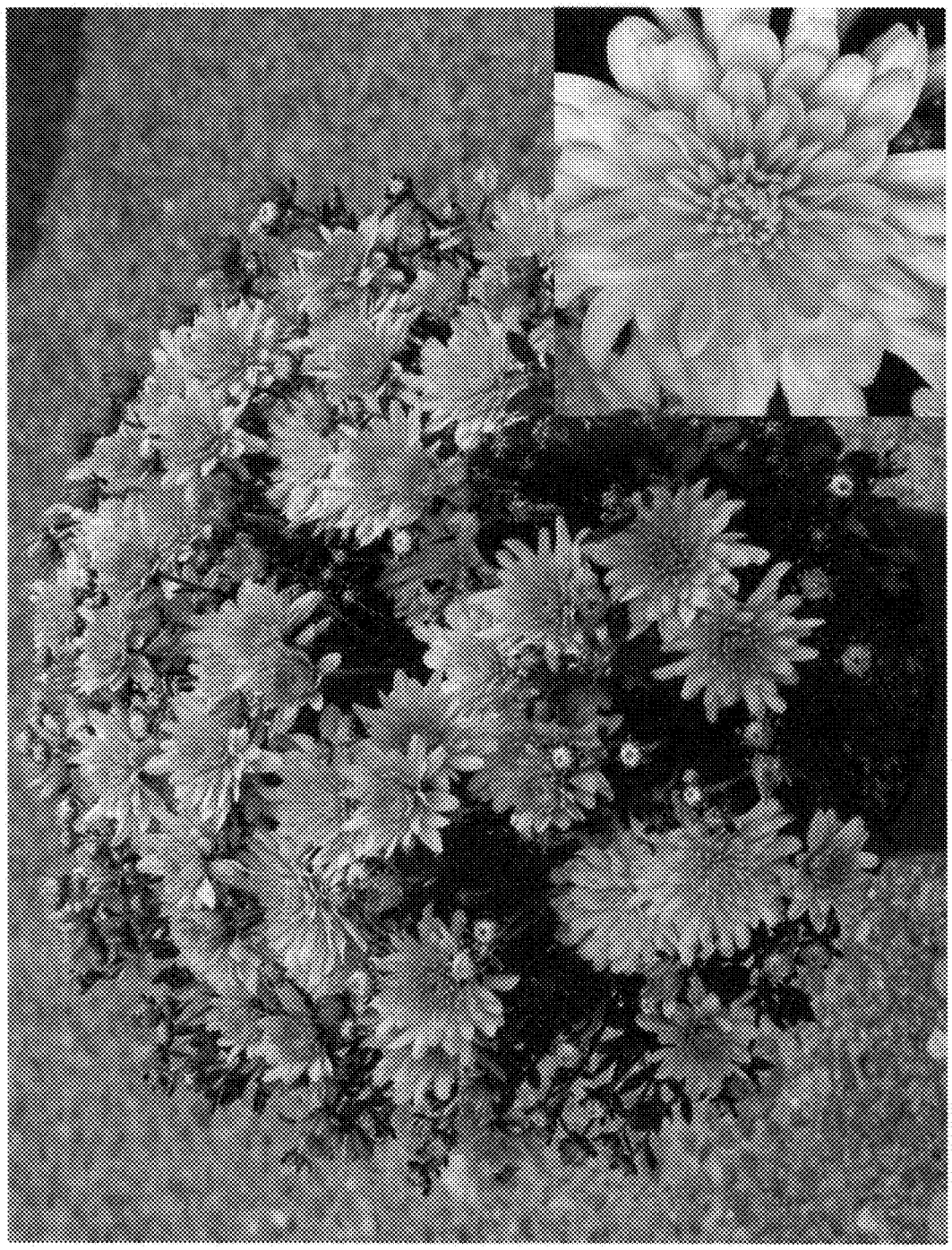

* * * * *